United States Patent [19]
Leopoldi et al.

[11] 4,258,714
[45] Mar. 31, 1981

[54] EAR SYRINGE

[76] Inventors: Norbert Leopoldi, 4180 Marine Dr., Chicago, Ill. 60613; William P. Heinrich, 2709 W. Sterling Dr., McHenry, Ill. 60050

[21] Appl. No.: 105,280

[22] Filed: Dec. 19, 1979

Related U.S. Application Data

[63] Continuation of Ser. No. 971,508, Dec. 20, 1978, abandoned.

[51] Int. Cl.$^3$ .............................................. A61M 1/00
[52] U.S. Cl. ................................... 128/232; 128/239
[58] Field of Search ................ 128/232, 239, 251, 248

[56] References Cited

U.S. PATENT DOCUMENTS

| | | | |
|---|---|---|---|
| 268,805 | 12/1882 | Knight | 128/232 |
| 1,242,806 | 10/1917 | Hohein | 128/239 X |
| 1,676,057 | 7/1928 | Slusser | 128/239 |
| 2,869,545 | 1/1959 | Forsyth | 128/232 |

FOREIGN PATENT DOCUMENTS

| | | | |
|---|---|---|---|
| 2603279 | 8/1977 | Fed. Rep. of Germany | 128/231 |
| 20458 | 11/1897 | United Kingdom | 128/232 |

*Primary Examiner*—John D. Yasko
*Attorney, Agent, or Firm*—McWilliams, Mann & Zummer

[57] ABSTRACT

This invention relates to an ear syringe having a built-in pressure regulator valve to control the discharge velocity of fluid issuing from the nozzle of the syringe, regardless of the amount of pressure applied on the bulb of the syringe, to prevent pain in the ear of a user, or possible damage to the ear as a result of squeezing the bulb too hard, or applying a sudden excessive pressure to the bulb.

3 Claims, 2 Drawing Figures

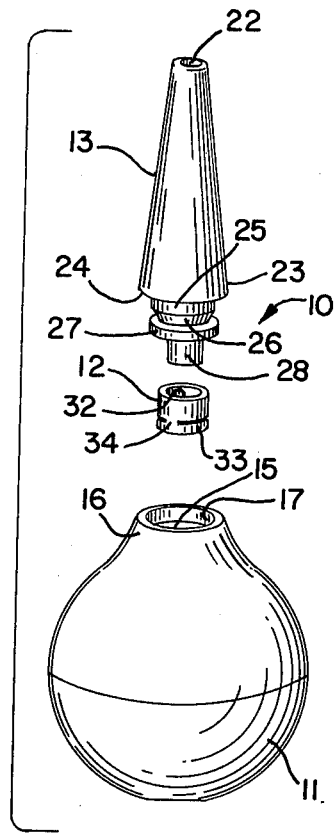
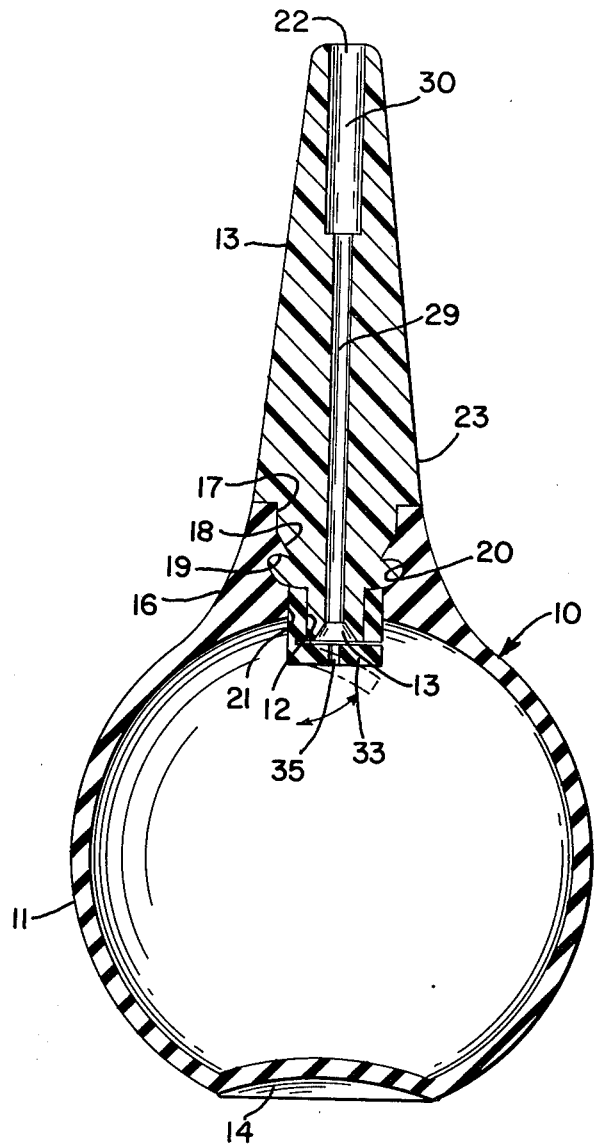

EAR SYRINGE

This is a continuation of application Ser. No. 971,508, filed Dec. 20, 1978, now abandoned.

BACKGROUND OF THE INVENTION

Bulb type ear syringes are quite common in the prior art and consist of a bulb for containing a fluid and a stem for entering the outer ear cavity to inject the fluid for flushing out the ear to remove foreign material, or hardened ear wax. In the typical syringe of this type the stem was usually integral with the bulb and being of the same material was generally soft and flexible. However, bulb syringes of this type did not include any means for regulating the pressure of fluids discharged from the bulb through the stem into the ear and the only means of controlling this discharge pressure was for the user carefully to squeeze the bulb very gently to keep the discharge pressure to a minimum in order to avoid discomfort and pain in the ear. In spite of such care it frequently occurred that too much pressure would be applied and often so suddenly that the result was not only pain and discomfort in the ear but sometimes real damage to the ear and especially the ear drum. Such syringes were not restricted to sale to doctors only but were generally available to the public in drug stores and other stores so that anyone could purchase a syringe of this type and use it without any supervision, or proper instructions as to any safety precautions to be exercised. The syringes constituted nothing more than a pressure bulb and a stem with an unrestricted outlet which enabled the bulb contents to be ejected in the form of an uncontrolled jet when the bulb was squeezed too vigorously particularly when used by a parent administering to a young child.

SUMMARY OF THE INVENTION

This invention provides an ear syringe of the bulb type but which incorporates a pressure regulating control which acts automatically as a safety device to positively control the discharge pressure and prevent excessively high pressures from being developed in the fluid stream issued through the nozzle. The syringe includes a more or less typical pressure bulb and a separate discharge stem but incorporating a special valve operative between the bulb and the discharge outlet through the stem to control the fluid pressure in the stem and thereby prevent a stream from being discharged through the stem at any velocity such as may be damaging to a persons ear. The valve is such that the syringe may be operated to draw fluid into the bulb without any restriction to the inwardly directed flow but automatically operates to reduce the outward flow under pressure from the bulb when the bulb is squeezed. The restriction to flow provided by the valve is such that the stream issuing through the stem is reduced to safe low levels of velocity and maintained constant at this safe level regardless of the amount of pressure exerted on the bulb. Further, the stem structure is such that a low pressure chamber is provided adjacent to the discharge outlet whereby the fluid stream issuing through the stem breaks up into droplets that also serve to maintain the fluid discharge at a relatively safe low pressure level.

OBJECTS OF THE INVENTION

The primary purpose of the invention is to provide a bulb type ear syringe having discharge pressure regulation controlled at a relatively low level.

The principal object of the invention is the provision of a bulb type ear syringe incorporating a pressure regulating valve between the bulb and discharge stem.

An important object of the invention is to provide a bulb type ear syringe having a separate stem with a pressure control valve operative between the bulb and the stem.

Another object of the invention is the provision of a bulb type ear syringe having a pressure control valve operative to regulate outgoing but permitting unrestricted inward flow.

A further object of the invention is to provide a bulb type ear syringe having a control valve regulating discharge pressure through a stem and having a low pressure chamber in the stem which breaks up the fluid flow into droplets.

A still further object of the invention is the provision of a bulb type ear syringe having a bulb and a separate stem with a separate valve member installed between the bulb and the stem to regulate fluid pressure through the stem.

Still another object of the invention is to provide a bulb type ear syringe having a pressure regulating control valve of cylindrical form to fit around the inner end of a stem within the pressure bulb and having a bottom flap which swings open on inward flow but closes on a build-up of pressure and has a restricted opening through the flap which regulates outward flow.

DESCRIPTION OF THE DRAWINGS

The foregoing and other and more specific objects of the invention are attained by the construction and arrangement of the bulb syringe illustrated in the accompanying drawings wherein FIG. 1 is an exploded perspective view of a bulb type ear syringe constructed in accordance with the teachings of this invention showing the three separate parts thereof consisting of the pressure bulb, the pressure regulating valve and the separate stem; and FIG. 2 is a vertical cross sectional view through the assembled syringe showing the stem and valve installed in the bulb with the valve shown closed and indicated in dotted lines in an open position for drawing in fluid.

DESCRIPTION OF PREFERRED EMBODIMENT

As clearly shown in FIG. 1, the ear syringe 10 is preferably made from three parts comprised of a bulb 11, a valve 12 and a stem 13. The bulb 11 may be made from a vinyl, or a suitable rubber compound that provides the flexibility required to provide for the bulb to be squeezed, or compressed, to draw in fluid when released and to discharge such fluid when it is again compressed. The valve 12 also may be made from vinyl, or rubber, in order to provide the flexibility necessary for operation of a flap valve incorporated as an integral part of the valve. The stem, or nozzle 13, may be formed from polypropylene or polyethylene. However, if it is desired that the nozzle be transparent it can be made of styrene and when it may be desirable to make the nozzle opaque it can be formed of an acrylic.

The bulb 11 may be generally typical of syringe bulbs of this type and is sufficiently flexible to admit of its being compressed by hand squeezing in the operations of both filling the syringe with fluid and in the discharge thereof when using the syringe to flush out an ear. The bulb is generally spherical but has a concavity 14 on the bottom end which provides an area for standing the syringe upright when not being used. The top of the bulb, as viewed in the drawings, has an opening 15 into which both the control valve 12 and the inner end of the stem, or nozzle 13, are received. The bulb has an upwardly projecting portion 16 in which the opening 15 is formed and in which the stem 13 is mounted. The opening 15, are formed in the projection 16, has an upper cylindrical inner surface 17 and immediately beneath this cylindrical entrance an inwardly and downwardly tapering surface 18 overlies a downwardly facing shoulder 19, which has a generally channel shaped groove 20 beneath the shoulder. The opening 15 into the bulb interior is completed by a cylindrical surface 21.

The stem, or nozzle 13, tapers generally from its mounting in the bulb opening 15 to its discharge opening 22 at the tip of the stem. The bulb end 23 of this stem is disposed flush with the outer surface of the projection 16, as best shown in FIG. 2 and includes a mounting portion which projects into and complements the various internal surfaces of the opening 15. A shoulder 24 immediately beneath the end 23 bears upon the top edge of the bulb opening and a cylindrical surface 25 fits closely within the bulb openings as defined by the surface 17. A tapering surface 26 on the stem engages the tapering surface 18 in the bulb opening while an outwardly extending annular collar 27 on the stem engages in the groove 20 under the shoulder 19 so that the stem 13 is securely interlocked with the bulb and retained in the bulb opening 15 by this engagement and is prevented from being separated from the bulb under any amount of pressure resulting from manual squeezing of the bulb to discharge its contents.

The bottom end of the stem is completed by an inwardly extending cylindrical stub 28 which projects into the interior of the bulb 11. A fluid passage 29 extends through the nozzle 13 and terminates in an expansion, or low pressure chamber 30 adjacent to the tip of the nozzle. The inner end of this fluid passage has a flared opening as at 31.

The automatic safety valve 12 fits directly onto the stub end 28 of the nozzle 13 within the cylindrical bottom portion 21 of the bulb opening 15. The valve includes vertical wall portions 32 which fit closely around the stub 28 and just as closely within the cylindrical area 21 of the bulb. A bottom flap valve 33 is formed integrally with the cylindrical walls 32 by a connecting portion 34 which acts as a hinge for the movements of the flap 33 between closed and open positions. This valve is open only when the bulb is being filled and this position is indicated by dotted lines in FIG. 2. During filling, the flap 33 swings inwardly under the inward flow of fluid when the compressed bulb is released to draw in the fluid but when the bulb is filled to the extent desired and then squeezed again, the flap 33 immediately swings to the closed position against the bottom end of the stub 28 and the cylindrical walls 32 so that the passage of fluid is restricted to that permitted through a small opening 35 through the center of the flap 33 directly in line with the fluid passage 29 through the nozzle.

The size of the hole 35, on the order of 0.030" as shown, is such that the flow of fluid from the nozzle 13 cannot exceed a predetermined rate of flow, or velocity, that has been found to be safe and tolerated by the human ear. This predetermined rate is held to the desired level by the restriction imposed by the size of the hole and cannot be exceeded no matter how much pressure is applied on the bulb 10 and regardless of whether such pressure is applied to the bulb suddenly, or steadily and relentlessly. In all circumstances the restriction 35 permits flow of the fluid from the bulb into the nozzle at the rate for which the restriction is designed. After passing through the restriction 35 there is an immediate drop in fluid pressure and upon entering the nozzle 13 the fluid flows through the passage 29 into the low pressure chamber 30 where the fluid breaks up into droplets because of the relative drop in pressure and this results in a further pressure drop which softens the fluid flow issuing from the tip 22 of the nozzle and avoids any possibility of discharging a stream at unsafe velocity.

From the foregoing it will be seen that an improved ear syringe has been provided that prevents damage to a persons ear by controlling the velocity and volume of the fluid stream issuing from the nozzle of the syringe. The bulb type syringe permits free flow of fluid for filling the syringe but immediately restricts the volume and pressure upon actuation to discharge fluid from the syringe whereby fluid issues from the nozzle at relatively low velocity.

What is claimed is:

1. An ear syringe including a compressible bulb and a nozzle, a restriction between the interior of the bulb and the nozzle, said nozzle having means comprising an expansion chamber which reduces the velocity of fluid discharged from the bulb through the nozzle, said expansion chamber being open adjacent to the discharge end of the nozzle, an opening in said bulb, said nozzle mounted in said opening, said restriction including a valve at the inner end of said nozzle mounted at least partially within said opening, said valve including an inner flap member movable between an open fill position and a closed discharge position, and an opening of predetermined size through the flap member effective in the closed position to restrict fluid flow to said expansion chamber and to reduce the velocity of fluid discharged through the open end of the nozzle.

2. An ear syringe as set forth in claim 1 wherein said nozzle includes a fluid passage therethrough and said opening communicates with said passage, and a low pressure chamber in the nozzle, said passage being in direct communication with said chamber.

3. An ear syringe as set forth in claim 1 wherein said nozzle is formed from a relatively rigid plastic material such as polypropylene or polyethylene, and said valve is made from a relatively softer material such as vinyl or rubber.

* * * * *